(12) United States Patent
Yamamoto et al.

(10) Patent No.: US 6,475,631 B1
(45) Date of Patent: Nov. 5, 2002

(54) ANTIMICROBIAL AGENT, ANTIMICROBIAL RESIN COMPOSITION AND ANTIMICROBIAL ARTIFICIAL MARBLE

(75) Inventors: Noriyuki Yamamoto, Nagoya (JP); Koji Sugiura, Nagoya (JP); Satoshi Yamato, Handa (JP)

(73) Assignee: Toagosei Co., Ltd., Tokyo (JP)

( * ) Notice: Subject to any disclaimer, the term of this patent is extended or adjusted under 35 U.S.C. 154(b) by 0 days.

(21) Appl. No.: 09/616,939

(22) Filed: Jul. 14, 2000

(30) Foreign Application Priority Data

Jul. 15, 1999 (JP) ............................... 11-201422
Jul. 10, 2000 (JP) ....................... 2000-207781

(51) Int. Cl.⁷ .................... B32B 27/30; B32B 27/36; A01N 59/00; A01N 59/14; A01N 59/26
(52) U.S. Cl. .................. 428/480; 428/482; 428/483; 428/522; 106/15.05; 106/18.26; 106/18.27; 106/18.3; 106/18.31; 106/18.36; 424/600; 424/601; 424/604; 424/606; 424/617; 424/641; 424/650; 424/657; 424/660; 424/682; 424/688; 424/691; 424/724
(58) Field of Search ................. 428/480, 482, 428/483, 522; 106/15.05, 18.26, 18.3, 18.27, 18.31, 18.36; 424/600, 601, 604, 606, 617, 641, 650, 657, 660, 677, 682, 688, 691, 692, 693, 724

(56) References Cited

FOREIGN PATENT DOCUMENTS

| | | | |
|---|---|---|---|
| EP | 0 837 836 B1 | * | 5/1999 |
| JP | 07-080978 | * | 3/1995 |
| JP | 07-257938 | | 10/1995 |
| JP | 07-266522 | | 10/1995 |
| JP | 8-175843 | | 7/1996 |
| JP | 9-071727 | | 3/1997 |
| JP | 09-295368 | * | 11/1997 |
| JP | 11-029343 | | 2/1999 |
| JP | 11-060268 | | 3/1999 |
| JP | 11-100227 | | 4/1999 |
| JP | 11-100228 | | 4/1999 |

* cited by examiner

Primary Examiner—Vivian Chen
(74) Attorney, Agent, or Firm—Oblon, Spivak, McClelland, Maier & Neustadt, P.C.

(57) ABSTRACT

The present invention provides an antimicrobial agent consisting of glass which comprises 50 to 60 mole % of ZnO, 20 to 30 mole % of at least one member selected from the group consisting of $B_2O_3$ and $P_2O_5$, 1 to 10 mole % of at least one member selected from the group consisting of $Al_2O_3$ and $ZrO_2$, 5 to 10 mole % of an alkali metal oxide and 0 to 15 mole % of $SiO_2$ and an antimicrobial agent consisting of glass which comprises 50 to 70 mole % of ZnO, 20 to 35 mole % of $P_2O_5$, 0.5 to 10 mole % of $Al_2O_3$, 0.5 to 10 mole % of $SnO_2$, 0 to 5 mole % of $SiO_2$ and 5 to 10 mole % of an alkali metal oxide as well as an antimicrobial resin composition and antimicrobial artificial marble, each of which comprises a resin and the antimicrobial agent blended therewith. The antimicrobial resin composition and the antimicrobial artificial marble are excellent in their antimicrobial properties, resistance to color change and water resistance.

16 Claims, No Drawings

ANTIMICROBIAL AGENT, ANTIMICROBIAL RESIN COMPOSITION AND ANTIMICROBIAL ARTIFICIAL MARBLE

BACKGROUND OF THE INVENTION

1. Field of the Invention

The present invention relates to an antimicrobial agent which comprise glass containing zinc oxide in a high concentration, an antimicrobial resin composition containing the agent and antimicrobial artificial marble.

The antimicrobial agent of the present invention has a high antimicrobial effect and hardly causes any discoloration with time during processing, storing and practically using the same. Therefore, the antimicrobial agent can be incorporated into a variety of high molecular weight compounds to obtain an antimicrobial resin composition showing antifungal properties, anti-algal properties and antimicrobial properties. The antimicrobial resin composition can be processed and used as, for instance, fibrous goods, paint and varnish products and molded articles.

The antimicrobial artificial marble of the present invention is a molded article of a resin mainly comprising a (meth) acrylic resin or an unsaturated polyester resin in which the antimicrobial agent of the present invention is incorporated. Alternatively, the antimicrobial artificial marble is a molded article comprising a base resin, which comprises a (meth) acrylic resin or an unsaturated polyester resin, and a gel coat layer of the antimicrobial agent of the present invention and a (meth) acrylic resin or an unsaturated polyester resin, applied to the surface of the base resin.

2. Details of Prior Art

There have conventionally been known such inorganic antimicrobial agents as those comprising antimicrobial metals such as silver, copper or zinc supported on, for instance, apatite, zeolite, glass, zirconium phosphate or silica gel. These inorganic antimicrobial agents have high safety and do not undergo any volatilization and decomposition as compared with organic antimicrobial agents. Therefore, the inorganic antimicrobial agents show a long-lasting or sustained antimicrobial effect and excellent heat resistance. For this reason, these antimicrobial agents are incorporated into a variety of high molecular weight compounds to form antimicrobial resin compositions, the resulting resin compositions are formed into antimicrobial processed articles such as fibrous and film-like articles or various molded articles, which have been used in various fields.

Among these inorganic antimicrobial agents, those comprising glass containing antimicrobial metals such as silver, copper or zinc have such characteristic properties that the particle sizes and refractive indexes of the agents and the ability thereof to release antimicrobial metals can, for instance, be easily controlled depending on the intended purposes. Accordingly, they are incorporated into a variety of resin compositions while making the most use of the foregoing characteristic properties.

In general, an antimicrobial agent consisting of antimicrobial metal-containing glass and a resin-molded article containing the agent have a tendency of getting colored when they are heated or exposed to ultraviolet rays. This tendency is conspicuous if the antimicrobial agents comprise glass containing silver or copper.

Among the antimicrobial metals, zinc is a metal whose coloration is relatively difficult. Accordingly, there have been proposed antimicrobial agents comprising glass containing zinc in a high concentration (Japanese Un-Examined Patent Publication (hereunder referred to as "J. P. KOKAI") Nos. Hei-7-257938, Hei 8-175843, Hei 11-29343, Hei 11-60268, Hei 11-100227 and Hei 11-100228).

There is disclosed, in J. P. KOKAI No. Hei 7-257938, an antimicrobial agent comprising soluble glass, which contains 15 to 50 mole % of ZnO, 40 to 80 mole % of $B_2O_3$ and 5 to 30 mole % of $Na_2O$.

J. P. KOKAI No. Hei 8-175843 discloses an antimicrobial agent consisting of glass, which comprises 40 to 55 mole % of $P_2O_5$, 35 to 45 mole % of ZnO, 5 to 15 mole % of $Al_2O_3$ and 1 to 10 mole % of $B_2O_3$ and an antimicrobial agent comprising the foregoing glass and $Ag_2O$ in an amount of 0.01 to 1.0% by weight per 100 parts by weight of the glass. The antimicrobial agent consisting of the foregoing glass is insufficient in the antimicrobial power and therefore, it is preferred to incorporate $Ag_2O$ into the glass antimicrobial agent. However, the $Ag_2O$-containing antimicrobial agent has a tendency of getting colored pale brown when irradiated with ultraviolet rays.

J. P. KOKAI No. Hei 11-29343 proposes antimicrobial glass powder of $ZnO$—$B_2O_3$—$SiO_2$ type one (25 to 80 mole % ZnO, 5 to 50 mole % $B_2O_3$, 1 to 70 mole % $SiO_2$; the total content of these three components ranges from 72.5 to 100 mole %, in Examples 1 to 9) whose $Na_2O$ content is not more than 4 mole %. In this patent, it is intended to improve the appearance of resin articles admixed with the glass powder or to eliminate any rough feeling and any reduction of the gloss due to changes with time by limiting the $Na_2O$ content to not more than 4 mole %. In respect of the composition of the antimicrobial agent, however, it comprises only a small amount of alkali metal ions, which serve as a component for modifying the network of glass. Therefore, the solubility of glass is low and there is sufficient room for improvement in antimicrobial property.

J. P. KOKAI No. Hei 11-60268 discloses antimicrobial glass having the following composition, as expressed in terms of "% by weight": 55 to 65% ZnO, 18 to 30% $B_2O_3$, 8 to 20% $SiO_2$, 0 to 10% MgO and 0 to 6% $Na_2O$.

J. P. KOKAI No. Hei 11-100227 discloses an antimicrobial agent consisting of $ZnO$—$P_2O_5$ type glass having the following composition as expressed in terms of "mole %": 46 to 80% ZnO, 5 to 50% $P_2O_5$, 0 to 30% $B_2O_3$+$SiO_2$, 0 to 40% RO (wherein RO is at least one member selected from the group consisting of MgO, CaO, SrO and BaO), 0 to 20% $R_2O$ (wherein $R_2O$ is at least one member selected from the group consisting of $Li_2O$, $Na_2O$ and $K_2O$).

J. P. KOKAI No. Hei 11-100228 discloses an antimicrobial agent consisting of $ZnO$—$P_2O_5$ type glass having the following composition as expressed in terms of "mole %": 25 to 70% ZnO, 5 to 40% $P_2O_5$, 0 to 35% $B_2O_3$, 0 to 20% $SiO_2$, 0 to 30% MgO, 0 to 30% CaO, 0 to 20% SrO, 0 to 15% BaO, 0 to 25% $Li_2O$, 0 to 25% $Na_2O$, 0 to 25% $K_2O$, 0 to 20% $TiO_2$, 0 to 10% $ZrO_2$, 0 to 20% $La_2O_3$ and 0 to 15% $Al_2O_3$.

The foregoing antimicrobial agents consisting of glass containing zinc oxide in a high concentration have a tendency of reducing their antimicrobial power observed after immersion thereof in warmed water and therefore, there is still room for improvement in water resistance.

The artificial marble has widely been used as a construction material excellent in heat resistance, water resistance, wear resistance and aesthetic appearance in, for instance, kitchen counters, washing stands, and goods for toilets and bathrooms. Most of these products are used in water-circulated environment, which is susceptible for the growth of bacteria and molds. For this reason, there has been a great need for the impartment of a function for preventing any adhesion of bacteria and molds and a function for inhibiting any growth thereof to the artificial marble. In particular in, for instance, hospitals, schools and public facilities, which are used by many and unspecified persons, there has also intensively been desired for the impartment of antimicrobial effect to the artificial marble, while taking into consideration a risk of the nosocomial infection with methicillin resistant Staphylococcus aureus (MRSA) and mass food poisoning due to coliform bacillus O-157.

To respond to these social requirements, there have been tried, for instance, the incorporation of an antimicrobial agent into the artificial marble or the application thereof onto the surface of the marble. In general, the antimicrobial agents can roughly be divided into organic and inorganic ones, but it would be doubtful whether the former has sufficient long-lasting antimicrobial effect and safety. On the other hand, the latter is excellent in these properties. However, most of the inorganic antimicrobial agents practically used comprise silver as a component for ensuring a high antimicrobial effect. Therefore, products prepared from resins to which these antimicrobial agents are added suffer from such a problem caused by silver ions that they may undergo color change during processing or with time during long-term storage or usage thereof.

The artificial marble may frequently be exposed to water, hot water, a variety of food stuffs, various detergents and/or heat and therefore, the artificial marble, which contains a silver-containing inorganic antimicrobial agent is particularly susceptible to color change. As a means for alleviating this tendency, there has been known a method in which silver is stabilized by selecting a specific carrier having strong bonding strength and bonding silver ions to the carrier to thus prevent any discoloration of the antimicrobial agent. In this case, however, the antimicrobial agent comprises silver and accordingly, it would be impossible to completely inhibit the color change of the agent. Alternatively, there has been proposed a method in which the silver-containing antimicrobial agent per se is encapsulated, but this method suffers from a problem such that the antimicrobial effect of the resulting agent is reduced.

On the other hand, as artificial marble, which makes use of an antimicrobial agent free of any silver, J. P. KOKAI No. Hei 7-266522 discloses those provided with, on the surface, a gel coat layer to which zinc-substituted zeolite is added and J. P. KOKAI No. Hei 9-71727 proposes artificial marble whose resin component includes zinc oxide. Moreover, J. P. KOKAI No. Hei 7-257938 proposes artificial marble whose resin component contains zinc-containing antimicrobial glass and is free of any silver. However, there still is room for improvement in antimicrobial property in the artificial marble to which these antimicrobial agents are added and the artificial marble containing such an antimicrobial agent has a tendency of causing whitening when exposed to warmed water.

Gist of the Invention

It is an object of the present invention to provide an antimicrobial agent consisting of glass, which shows excellent antimicrobial effect when incorporated into a resin and which is also excellent in the resistance to color change and water resistance of the resin containing the agent, as well as an antimicrobial resin composition and antimicrobial artificial marble, which comprise the antimicrobial agent.

Accordingly, the antimicrobial agent of the present invention consists of glass which comprises 50 to 70 mole % of ZnO, 20 to 50 mole % of at least one member selected from the group consisting of $B_2O_3$ and $P_2O_5$, 0.5 to 15 mole % of at least one member selected from the group consisting of $Al_2O_3$ and $ZrO_2$, 5 to 10 mole % of an alkali metal oxide and 0 to 20 mole % of $SiO_2$; or glass which comprises 50 to 70 mole % of ZnO, 20 to 35 mole % of $P_2O_5$, 0.5 to 10 mole % of $Al_2O_3$, 0.5 to 10 mole % of $SnO_2$, 0 to 5 mole % of $SiO_2$ and 5 to 10 mole % of an alkali metal oxide.

The antimicrobial resin composition comprising the antimicrobial agent of the present invention is useful as a raw material for a variety of resin-molded articles and the resin-molded articles to which the antimicrobial agent of the present invention is added are excellent in antimicrobial properties, resistance to color change and water resistance.

The antimicrobial artificial marble obtained by incorporating the antimicrobial agent of the present invention into a (meth)acrylic resin or an unsaturated polyester resin and then molding the resulting resin composition can effectively be used in, for instance, kitchen counters, washing stands, goods for toilets and bathrooms and construction materials and any color change, with time, thereof is inhibited.

Preferred Embodiments

Antimicrobial Agent

The antimicrobial agents of the present invention can be divided into Type α and Type β. The antimicrobial agent of Type α consists of glass comprising 50 to 70 mole % of ZnO, 20 to 50 mole % of at least one member selected from the group consisting of $B_2O_3$ and $P_2O_5$, 0.5 to 15 mole % of at least one member selected from the group consisting of $Al_2O_3$ and $ZrO_2$, 5 to 10 mole % of an alkali metal oxide and 0 to 20 mole % of $SiO_2$.

ZnO is a component for imparting the antimicrobial properties to the antimicrobial agent of the present invention. The content of ZnO preferably ranges from 53 to 65 mole % and more preferably 55 to 60 mole %. If the content of ZnO exceeds 70 mole %, it is difficult to obtain stable glass, while if the content thereof is less than 50 mole %, the resulting antimicrobial agent has insufficient antimicrobial properties.

The content of the at least one member selected from the group consisting of $B_2O_3$ and $P_2O_5$ preferably ranges from 20 to 40 mole % and more preferably 25 to 35 mole %. If the content of the at least one member selected from the group consisting of $B_2O_3$, and $P_2O_5$ exceeds 50 mole %, the antimicrobial agent consisting of the glass according to the present invention has high solubility in water and this in turn impairs the antimicrobial properties, resistance to color change and water resistance of the glass. On the other hand, if the content is less than 20 mole %, it is difficult to obtain stable glass.

The content of the at least one member selected from the group consisting of $Al_2O_3$ and $ZrO_2$ preferably ranges from 1 to 10 mole %. If the content of the at least one member selected from the group consisting of $Al_2O_3$ and $ZrO_2$ exceeds 15 mole %, it is difficult to obtain stable glass. On the other hand, if the content thereof is less than 0.5 mole %, the water resistance and resistance to color change of the antimicrobial agent consisting of the glass according to the present invention are reduced.

Examples of the alkali metal oxides preferably used herein are $Li_2O$, $Na_2O$ and $K_2O$, with $Na_2O$ being particularly preferred. The content of the alkali metal oxide preferably ranges from 6 to 8 mole %. If the content of the alkali metal oxide exceeds 10 mole %, the resulting glass of the present invention has high solubility in water and this in turn impairs the sustained antimicrobial properties, resistance to color change and water resistance of the antimicrobial agent of the present invention. On the other hand, if the content thereof is less than 5 mole %, the solubility of the glass is conversely reduced and the antimicrobial agent never shows sufficient antimicrobial properties.

In the present invention, the essential glass-forming components are at least one member selected from the group consisting of $B_2O_3$ and $P_2O_5$ and at least one member selected from the group consisting of $Al_2O_3$ and $ZrO_2$, but other glass-forming components may, if desired, be added thereto. Preferred examples thereof include $SiO_2$ and $TiO_2$, with $SiO_2$ being particularly preferred. The content of the other glass-forming component is preferably not more than 20 mole % and more preferably not more than 15 mole %.

Moreover, components such as MgO, CaO and $CaF_2$ may if desired be incorporated into the glass. These so-called "modifying components" are effective for making the melting and molding of the glass easy. However, if the content thereof is high, the water resistance of the resulting glass may be reduced. Accordingly, the content thereof is preferably not more than 3 mole % and more preferably not more than 1 mole %.

The antimicrobial agent of Type β according to the present invention consists of glass which comprises, as components common to the agents of Type α and Type β, ZnO, $P_2O_5$, $Al_2O_3$, $SiO_2$ and an alkali metal oxide; and $SnO_2$ as other component. More specifically, the antimicrobial agent of Type β according to the present invention consists of glass which comprises 50 to 70 mole % of ZnO, 20 to 35 mole % of $P_2O_5$, 0.5 to 10 mole % of $Al_2O_3$, 0.5 to 10 mole % of $SnO_2$, 0 to 5 mole % of $SiO_2$ and 5 to 10 mole % of an alkali metal oxide. This is useful, in particular, as an antimicrobial agent excellent in resistance to warmed water.

In general, oxide components included in glass are divided into those forming the network structure of the glass, those modifying the network structure and present in the interstices of the network and those intermediate between them. Among the foregoing components, $P_2O_5$, $Al_2O_3$, $SnO_2$ and $SiO_2$ are glass network structure-forming components, ZnO is an intermediate component and the alkali metal oxide is a network structure-modifying component. It would be recognized that ZnO mainly contributes to the development of the antimicrobial power of the agent and that the alkali metal oxide makes the melting and molding of the glass easy and contributes to, for instance, the control of the solubility of the glass.

The content of ZnO preferably ranges from 53 to 65 mole % and more preferably 55 to 60 mole %. If the content of ZnO exceeds 70 mole %, it is difficult to obtain glass having stable network structure, while if the content thereof is less than 50 mole %, the resulting glass of the present invention possesses insufficient antimicrobial properties.

The content of $P_2O5$ preferably ranges from 25 to 30 mole %. If $P_2O_5$ is incorporated into the antimicrobial agent in an amount of more than 35 mole %, the resulting antimicrobial agent of the present invention has high solubility in water and the water resistance thereof is impaired. On the other hand, if the content thereof is less than 20 mole %, it is difficult to obtain stable glass.

The content of $Al_2O3$ and $SnO_2$ each preferably ranges from 2 to 7 mole %. In these cases, if the content exceeds 10 mole %, the solubility of the resulting glass is reduced and accordingly, the antimicrobial properties of the glass is also reduced. On the other hand, if the content is less than 0.5 mole %, it is difficult to obtain glass having a stable network structure. In addition, the appearance of the resin-molded article in which the antimicrobial agent is incorporated is impaired because of its rough surface.

Examples of preferred alkali metal oxides are $Li_2O$, $Na_2O$ and $K_2O$, with $Na_2O$ being particularly preferred. The content of the alkali metal oxide preferably ranges from 6 to 8 mole %. If the alkali metal oxide is added in an amount of more than 10 mole %, the resulting glass has extremely high solubility and the water resistance thereof is accordingly impaired. On the other hand, if the content is less than 5 mole %, the solubility of the glass is conversely too low and the glass never shows sufficient antimicrobial properties.

Examples of preferred and desired glass network structure-forming components in the antimicrobial agent of Type β are $SiO_2$, $ZrO_2$ and $TiO_2$, with $SiO_2$ being particularly preferred. The content of these desired glass network structure-forming components is preferably not more than 5 mole %.

When the antimicrobial agent of the present invention is incorporated into a resin, the agent is in general used in the form of powder and preferred powder is in general one having an average particle size of not more than 20 μm and a maximum particle size of not more than 50 μm from the viewpoint of dispersibility and processability. In case where the resulting resin composition is formed into, for instance, fibrous products, paints and varnishes and films, preferably used is one having an average particle size of not more than 5 μm and a maximum particle size of not more than 20 μm in order to prevent any reduction of physical properties of the resulting products.

Method for Preparing Antimicrobial Agent

The antimicrobial agent of the present invention can be prepared according to any known method. In general, a mixture of glass raw materials is melted in a melting furnace at 1000 to 2000° C., then the melt is quenched to give a glass product and the resulting massive glass is pulverized to thus easily obtain powdery glass.

The antimicrobial agent of the present invention can easily be prepared by melting a raw mixture having any composition falling within the range of the present invention at an appropriate melting temperature and then quenching the resulting melt using a quenching means adapted for the quenching characteristics of the melt.

To improve the quenching effect, it is effective to enlarge the contact area between the melt and the cooling body. For instance, a glass melt is passed through a pair of rotatable metal rollers cooled with a cooling medium such as water at a high speed to thus ensure an extremely high cooling effect. The use of this cooling method makes the vitrification of the glass melt extremely easy. In addition, if the glass melt is cooled by this method, the glass passed through the rollers is formed into a thin plate-like shape (for instance, a plate having a thickness ranging from several micrometers to several hundreds micrometers and preferably 10 to 100 μm) and therefore, the resulting glass may extremely easily be pulverized into powder.

Resins

A variety of antimicrobial resin articles can easily be obtained by incorporating the antimicrobial agent of the present invention into a variety of resins and then molding the resulting resin composition. Resins usable herein are not restricted to any specific one and may be natural, synthetic or semisynthetic resins or may be either thermoplastic or thermosetting resins. Specific examples of these resins may be resins for molding, resins for fibers or rubber-like resins such as polyethylene, polypropylene, vinyl chloride resin, ABS resin, AS resin, nylon resin, polyester, polyvinylidene chloride, polystyrene, polyacetal, polycarbonate, polybutylene terephthalate (PBT), acrylic resin, fluoroplastic, polyurethane elastomer, polyester elastomer, melamine, urea resin, tetrafluoroethylene resin, unsaturated polyester resin, rayon, acetate, polyvinyl alcohol, cuprammonium rayon, triacetate, vinylidene, natural rubber, silicone rubber, styrene-butadiene rubber, ethylene-propylene rubber, fluororubber, nitrile rubber, chlorosulfonated polyethylene rubber, butadiene rubber, synthetic natural rubber, butyl rubber, urethane rubber and acryl rubber.

The rate of the antimicrobial agent incorporated into the antimicrobial resin articles preferably ranges from 0.01 to 10 parts by weight and more preferably 0.1 to 5 parts by weight per 100 parts by weight of the antimicrobial resin composition. If the rate of the antimicrobial agent is less than 0.01 part by weight, the resulting antimicrobial resin article may have insufficient antimicrobial properties, while if the rate thereof exceeds 10 parts by weight, any further improvement of the antimicrobial effect cannot be expected.

To improve the dispersibility of the antimicrobial agent in the antimicrobial resin article, it is preferred that an intermediate product called master batch whose content of the antimicrobial agent is higher than that in the final antimicrobial resin article is first prepared, then a straight resin free of any antimicrobial agent is added to the master batch and the resulting mixture is then formed into a desired article. In this case, the rate of the antimicrobial agent in the master batch preferably ranges from 10 to 200 parts by weight and more preferably 10 to 40 parts by weight per 100 parts by weight of the antimicrobial resin composition (master batch).

When the antimicrobial agent of the present invention is kneaded with a resin or fibers, the resin or fibers show their antimicrobial properties due to the antimicrobial agent exposed on the surface thereof. In this case, however, the antimicrobial agent may be removed when the resin or fibers are, for instance, rubbed, washed or cleaned. If the antimicrobial agent is removed to a considerable extent, the antimicrobial effect thereof is reduced and in some cases, the effect disappears within a very short period of time.

When the antimicrobial agent of the present invention is kneaded with, for instance, a resin, the antimicrobial agent is preferably subjected to a surface treatment with, for instance, a silane coupling agent in order to improve the adhesion of the antimicrobial agent to the resin and to prevent any removal of the antimicrobial agent.

In the present invention, it is sufficient to appropriately select an optimum surface-treating agent depending on, for instance, the applications of the resulting articles, kinds of resins used and processing methods. The surface-treating agent is not restricted to any specific one and may be any coupling agent conventionally used for the surface treatment of inorganic powder.

Specific examples of surface-treating agents are vinyl silanes such as vinyl triethoxysilane and vinyl trimethoxysilane; (meth)acryloxy silane or glycidoxy silane such as γ-(methacryloxypropyl)trimethoxy silane and γ-glycidoxypropyl trimethoxy silane; tetraethoxy silane, silicone oil, tetraisopropoxy titanium and aluminum ethylate.

The surface-treating method usable herein is not restricted to any particular one and may be any conventionally known method for surface-treating inorganic powder. Examples thereof include dry methods, wet methods, spraying methods and gasification methods.

The antimicrobial agent of the present invention may be used alone, but the antimicrobial properties thereof can further be improved by the use thereof in combination with, for instance, 5 to 30% by weight of a silver-containing inorganic antimicrobial agent. This would be due to the synergistic effect of two different kinds of antimicrobial components present in the glass, i.e., zinc ions and silver ions in the silver-containing inorganic antimicrobial agent.

In addition, the antimicrobial agent of the present invention is quite excellent in the effect of preventing any color change and therefore, the resulting resin articles never undergo any coloration and discoloration even when a silver-containing inorganic antimicrobial agent is used in combination with the antimicrobial agent of the present invention.

The silver-containing inorganic antimicrobial agents usable herein in combination with the antimicrobial agent of the present invention are not restricted to any particular one insofar as they are silver-supporting inorganic compounds. Examples of inorganic compounds for supporting silver ions are as follows:

More specifically, examples thereof include inorganic adsorbents such as active alumina and silica gel, and inorganic ion-exchangers such as zeolite, calcium phosphate, zirconium phosphate, titanium phosphate, potassium titanate, hydrous bismuth oxide, hydrous zirconium oxide and hydrotalcite.

Among these inorganic compounds, preferably used herein are inorganic ion-exchangers since they can firmly support silver ions, with silver-containing antimicrobial agents comprising zirconium phosphate and represented by the following general formula [1] in which M is Zr being particularly preferred:

$$Ag_a A_b M_2(PO_4)_3 \cdot nH_2O \qquad [1]$$

wherein A is at least one ion selected from the group consisting of alkali metal ions, alkaline earth metal ions, ammonium ion and hydrogen ion; M is a tetravalent metal ion, a and b each represents a positive number, provided that a+mb=1; m represents the valence of A; and n is a number satisfying the relation: $0 \leq n \leq 6$.

Various other additives may if necessary be added to the antimicrobial agent of the present invention in order to improve the ability of kneading with resins and other physical properties thereof. Specific examples of such additives are pigments, dyes, antioxidants, light stabilizers, flame-retardants, antistatic agents, foaming agents, impact resistant reinforcing agents, glass fibers, metal soaps, moisture-proofing agents and extending agents, coupling agents, flowability-improvers, deodorants, wood powder, stain-proofing agents, and rust-proofing agent. An organic antimicrobial and antifungal agent may additionally be added to the antimicrobial agent to improve the quick-acting ability of the effect and antifungal effect.

Examples of preferred organic antimicrobial and antifungal agents to be admixed with the antimicrobial agent of the present invention are quaternary ammonium salt compounds, fatty acid ester compounds, biguanide compounds, 2-bromo-2-nitro-1,3-propanediol (Pronopol), phenolic compounds, anilide compounds, iodine-containing compounds, imidazole compounds, thiazole compounds, isothiazolone compounds, triazine compounds, nitrile compounds, fluorine-containing compounds, chitosan, tropolone compounds and organometal compounds (zinc pyrithione), 10,10'-oxybisphenoxasine (OBPA)).

Any conventionally known method can be used for incorporating the antimicrobial agent into a resin. Examples thereof include (i) a method comprising directly mixing, in a mixer, the powdery antimicrobial agent with a pellet resin or a powdery resin while using a spreading agent for facilitating the adhesion of the powder to the resin and a dispersant for improving the dispersibility of the powdery antimicrobial agent; (ii) a method comprising the steps of mixing raw materials in the same manner used above, forming the resulting mixture into pellets using an extrusion molding machine and then incorporating the resulting molded product into a pellet resin; (iii) a method comprising the steps of forming the antimicrobial agent into pellets having a high concentration of the agent using a wax and then incorporating the resulting molded product into a pellet resin; and (iv) a method comprising the steps of dispersing and mixing the antimicrobial agent in a liquid substance having a high viscosity such as a polyol to give a paste composition and then incorporating the composition into a pellet resin.

The molding of the foregoing antimicrobial resin composition can be carried out using any known processing technique and machine depending on the characteristic properties of various resins used. Thus, the antimicrobial agent and the resin can be mixed, blended or kneaded with each other at an appropriate heating temperature or a pressure to thus easily give a molded body. More specifically, these operations may be performed in the usual manner and the resin composition can be formed into a variety of shapes such as mass, sponge, film, sheet, thread or pipe shapes or any combination thereof.

In the antimicrobial resin-molded article thus prepared, the antimicrobial agent as a component thereof has excellent antimicrobial properties and resistance to color change and therefore, any deterioration is not observed during blending the antimicrobial agent and a resin, and during storage and usage of the antimicrobial resin composition, subsequent to the blending operation.

The shape of the antimicrobial agent of the present invention is not particularly limited to any specific one and may thus appropriately be mixed with other components and/or may be used in the form of a composite with other materials. For instance, the antimicrobial agent can be used in a variety of shapes such as powder, powder-dispersed liquids, particulate, paint and varnishes, fiber, paper, film, and aerosol.

Applications

The antimicrobial resin composition containing the antimicrobial agent of the present invention can be used in various fields, wherein antifungal, anti-algal and antimicrobial properties are required, such as electric appliances, kitchen appliances, fibrous products, dwelling construction materials, toiletry goods, paper goods, toys, leather goods, writing materials, as well as other goods.

More specifically, examples of applications include electric appliances such as dish washing machines, dish dryers, refrigerators, washing machines, pots, televisions, personal computers, CD-radio-cassette players, cameras, video-cameras, water purifiers, rice cookers, vegetable cutters, registers, bedding dryers, facsimiles, ventilating fans and air conditioners; kitchen appliances such as tableware, chopping boards, straw cutters, trays, chopsticks, tea-things, vacuum bottles, kitchen knives, handles of tablespoons, fry-turning tools, lunch boxes, rice scoops, bowls, water-drainage cages, triangular drainage cages, containers for pot cleaners, garbage cages and water-draining bags.

Specific examples of fibrous products are shower curtains, wadding for bedding, filters for air conditioners, panty stockings, socks, wet towels, bed sheets, side fabrics for bedding, pillows, gloves, aprons, curtains, diapers, bandages, masks and sportswear. Examples of dwelling construction materials are decorative laminates, wall paper, alcove slabs, films for windows, handles or grips, carpets, mats, artificial marble, balustrades, joints, tiles and waxes. Examples of toiletry goods are seats for commodes, bathtubs, tiles, close stools, containers for filthy things, brushes for stools, covers for bathtubs, pumice stones, containers for soaps, seats for bath, cages for clothes, shower nozzles and washing stands. Examples of paper goods are drug packing paper, medicine cabinets, sketching books, clinical charts and colored paper used for making figures by folding. Examples of toys are dolls, stuffed toys, clayey paper, blocks and puzzles.

Furthermore, examples of leather goods are boots and shoes, bags, belts, wrist straps, interior goods, chairs, gloves and hand straps. Examples of writing goods include ball-point pens, propelling pencils, pencils, rubber erasers, crayons, blank forms, memorandum books, floppy disks, rulers, tags and staplers (paper fasteners). Examples of other goods are insoles, containers for cosmetics, pot cleaners or scrubbing brushes, puffs for cosmetics, hearing aids, musical instruments, filters for tobacco, adhesive paper sheets for cleaning, grips for hand straps, sponge, kitchen towels, cards, microphones, goods for barbers, automatic vending machines, razors, telephones, clinical thermometers, stethoscopes, slippers, cases for clothes, toothbrushes, sand for sandboxes, films for packaging foods and aerosols.

Antimicrobial Artificial Marble

Among the foregoing various applications, the antimicrobial agent of the present invention is useful, in particular, in the impartment of an antimicrobial power to artificial marble.

The antimicrobial artificial marble of the present invention includes products obtained by incorporating the antimicrobial agent into the whole resin composition for artificial marble and then curing the composition (this preparation method will hereunder be referred to as "bulk method") and products obtained by incorporating the antimicrobial agent only into a gel coat composition for forming the surface layer of artificial marble and applying a gel coat layer onto the surface of a base material for the artificial marble (this method will hereunder be referred to as "gel coat method"). In any case, the antimicrobial agent of the present invention is used by blending the same with a specific resin component suitable for preparing artificial marble. The antimicrobial agents of Type α and Type β may be used as those used for preparing artificial marble, but the antimicrobial agent of Typed β is particularly preferred.

The resin components constituting the artificial marble of the present invention are base materials for artificial marble or matrix resins for forming the gel coat layer and they may be (meth)acrylic resins or unsaturated polyester resins. In this respect, the term "(meth)acrylic" used herein means "acrylic and/or methacrylic".

The term (meth)acrylic resin means resins obtained by polymerizing various kinds of (meth)acrylic monomers. Specific examples of (meth)acrylic monomers are (meth)acrylic acid esters such as methyl (meth)acrylate, ethyl (meth)acrylate, butyl (meth)acrylate, 2-ethylhexyl (meth)acrylate and benzyl (meth)acrylate, glycidyl (meth)acrylate and melamine (meth) acrylate. Copolymerizable vinyl monomers may, if necessary, be used in combination with the (meth)acrylic monomers. Examples of such copolymerizable vinyl monomers are styrene, α-methyl styrene, vinyl toluene, acrylonitrile and vinyl acetate. The amount of the copolymerizable vinyl monomer to be used is preferably not more than 10 parts by weight per 100 parts by weight of the (meth)acrylic monomer.

Moreover, it is preferred to use a crosslinkable vinyl monomer having, in the molecule, a plurality of polymerizable double bonds, as a crosslinking agent for crosslinking the (meth)acrylic resins, in combination with the (meth)

acrylic monomers. Examples of such crosslinkable vinyl monomers are ethylene glycol di(meth)acrylate, diethylene glycol di(meth)acrylate, triethylene glycol di(meth)acrylate, tetraethylene glycol di(meth)acrylate, 1,6-hexanediol di(meth)acrylate, trimethylol propane tri(meth)acrylate, polybutylene glycol di(meth)acrylate and neopentyl glycol di(meth)acrylate. The amount of the crosslinkable vinyl monomer to be used in general ranges from 0.05 to 20 parts by weight per 100 parts by weight of the (meth)acrylic monomer.

Furthermore, it is also preferred to use a mixture (hereunder referred to as "syrup") of the foregoing (meth) acrylic monomer and a polymer thereof as the (meth)acrylic resin in order to prevent any sedimentation of fillers such as aluminum hydroxide and to shorten the curing time of the resin component.

The unsaturated polyester resins used in the present invention are prepared by polycondensation of unsaturated polybasic acids or acid anhydrides thereof (if necessary, saturated polybasic acids or acid anhydrides thereof may be used in combination therewith) with polyhydric alcohols. Particularly preferred are unsaturated polyesters obtained by polycondensation of α,β-unsaturated dibasic acids or acid anhydrides thereof, aromatic saturated dibasic acids or acid anhydrides thereof and glycols.

Examples of such α,β-unsaturated dibasic acids or acid anhydrides thereof used for synthesizing the unsaturated polyesters are maleic acid, maleic anhydride, fumaric acid, itaconic acid, citraconic acid, chloromaleic acid and esters thereof Examples of glycols are ethylene glycol, propylene glycol, diethylene glycol, dipropylene glycol, 1,3-butanediol, 1,4-butanediol, 2-methylpropane-1,3-diol, neopentyl glycol, triethylene glycol, tetraethylene glycol, 1,5-pentanediol, 1,6-hexanediol, bisphenol A and hydrogenated bisphenol A.

Examples of saturated dibasic acids or acid anhydrides thereof optionally used in combination with the unsaturated dibasic acids or anhydrides thereof are aromatic acids and anhydrides thereof such as phthalic acid, phthalic anhydride, isophthalic acid, terephthalic acid and tetrahydrophthalic anhydride; and aliphatic acids and anhydrides thereof such as oxalic acid, malonic acid, succinic acid, adipic acid, sebacic acid and azelaic acid.

In addition, examples of unsaturated monomers for crosslinking the unsaturated polyester are styrene, vinyl toluene, α-methyl styrene, chlorostyrene, vinyl naphthalene, methyl vinyl ketone, methyl (meth)acrylate and ethyl (meth) acrylate.

It is, if necessary, preferred to add, to the foregoing (meth)acrylic resins or unsaturated polyester resins, a curing (polymerization) catalyst, a curing (polymerization) accelerator, a filler, a pigment, a dye, a flame-proofing agent, a releasing agent, a thickening agent or the like.

As such curing catalysts, there may be listed, for instance, tert-butyl peroxy maleic acid, benzoyl peroxide, methyl ethyl ketone peroxide, cumene hydroperoxide, tert-butylhydroxy peroxide and dicumyl peroxide. Examples of curing accelerators are cobalt naphthenate or the like.

Fillers may, for instance, be aluminum hydroxide, calcium hydroxide, magnesium hydroxide, talc, quartz, silica, zinc oxide, titanium oxide, clay and calcium carbonate, with aluminum hydroxide being particularly preferred.

Any known method can be adopted for the incorporation of the antimicrobial agent of the present invention into the resin composition for preparing artificial marble used in the bulk method or the resin composition for gel coating used in the gel coat method. For instance, the incorporation of the antimicrobial agent into these resin compositions can be carried out by adding a desired amount of the antimicrobial agent of the present invention to a resin composition for preparing artificial marble, then kneading and mixing them together using, for instance, a kneader, a mixer, a roll mill or an extruder to thus sufficiently disperse the agent in the resin composition.

The rate of the antimicrobial agent to be incorporated into the resin composition for artificial marble used in the bulk method or the resin composition for forming a gel coat layer used in the gel coat method preferably ranges from 0.05 to 10 parts by weight and more preferably 0.5 to 5 parts by weight per 100 parts by weight of each resin composition. If the rate of the agent is less than 0.05 part by weight, the resulting artificial marble may show insufficient antimicrobial properties. On the other hand, any further improvement in the antimicrobial effect cannot be expected even if the rate thereof exceeds 10 parts by weight.

Method for Preparing Antimicrobial Artificial Marble

According to the bulk method, the antimicrobial artificial marble of the present invention is prepared as follows: There are mixed together materials for a matrix resin, i.e., monomers for (meth)acrylic resin or unsaturated polyester resin, a curing catalyst and the antimicrobial agent of the present invention. If desired, inorganic fillers such as glass fibers, aluminum hydroxide, silica and/or silica gel, a crosslinking agent, a curing accelerator, a pigment or the like may be mixed with and dispersed in the foregoing mixture. The resulting mixture is casted into a mold and then cured at room temperature or with heating to give artificial marble. The mixture may likewise be molded by other molding methods such as injection molding and press molding in addition to the cast molding, but the cast molding is most preferred.

In case where the artificial marble has a gel coat layer on the surface of the base resin, the artificial marble is usually produced as follows. A resin composition for forming a gel coat layer, in which the antimicrobial agent of the present invention is dispersed, is first applied onto the mold for molding the artificial marble by for instance, the spray-up method and then cured. Subsequently, a composition for a base resin is casted into the mold and then cured. A laminate of the gel coat layer and the base resin is released from the mold to give artificial marble.

Operations of the Invention

It is presumed that the antimicrobial agent of the present invention exhibits excellent antimicrobial properties, resistance to color change and water resistance according to the following mechanism. That is, the glass of Type α comprises ZnO in a high concentration and simultaneously comprises an appropriate amount of an alkali metal oxide. Therefore, the glass has a proper solubility and thus it has a high antimicrobial effect and is excellent in the durability of the effect. Since the alkali metal oxide improves the solubility of the glass, the oxide has an effect of enhancing the antimicrobial effect, while it may reduce the water resistance and resistance to color change. However, the simultaneous use of $Al_2O_3$ and/or $ZrO_2$ permits the appropriate control of the solubility of the glass and in turn results in the preparation of glass which is excellent in the water resistance and resistance to color change.

In case of the glass of Type β of the present invention, the glass can easily and stably be prepared by incorporating an appropriate amount of $P_2O_5$, $Al_2O_3$ and $SnO_2$ as glass-forming components and the solubility of the resulting glass can appropriately be controlled by adjusting the composition thereof to such specific ones and this accordingly results in the preparation of glass excellent in the resistance to warmed water and resistance to color change. Moreover, the glass has a low hardness and can easily be pulverized into fine particles, as compared with the conventional glass antimicrobial agents. Therefore, the addition thereof never impairs the appearance of the resulting resin articles.

EXAMPLES

The present invention will hereunder be described in more detail with reference to the following Examples.

Example 1
(Preparation of Antimicrobial Agent (Type α))

Each raw preparation having a composition (mole %) specified in the following Table 1 (Sample Nos. α1 to α4) was melted by heating it to 1000 to 1400° C. to give glass, followed by wet pulverization of the resulting glass in a ball mill to thus prepare each corresponding antimicrobial agent consisting of glass particles having an average particle size of about 10 μm and a maximum particle size of 50 μm.

An antimicrobial agent (Sample No. α2: 5 kg) was introduced into a Henschel mixer, it was sprayed with 200 g of an ethanol solution containing 50 g of γ-aminopropyl trimethoxysilane with stirring, the antimicrobial agent was removed from the mixer and then subjected to heating at 120° C. for 12 hours to give a sample (Sample No. α9).

Comparative Example 1
(Preparation of Antimicrobial Agent)

The same procedures used in Example 1 were repeated except for using raw preparations having compositions (mole %) specified in the following Table 1 (Sample Nos. α5 to α8) to give antimicrobial agents consisting of glass.

resin composition was retained in the cylinder in its molten state for 5 minutes upon the injection molding thereof and then molded to confirm the color thereof.

By way of comparison, molded samples containing 0.3% by weight of the antimicrobial agent (Sample Nos. α5 to α8) and molded polystyrene resin (Sample No. α10) were likewise injection molded.

The antimicrobial powers of various polystyrene plate samples thus prepared were evaluated by the following method.

Staphylococcus aureus was used as test bacteria, a plate specimen having a size of 5 cm×5 cm was cut from each antimicrobial plate, a liquid containing the bacteria (0.5 ml) was dropped on the surface of each plate so that the number of bacterial cells per plate was equal to $10^5$ to $10^6$, the plate was covered with a polyethylene film of 4.5 cm×4.5 cm to thus uniformly bring the film into contact with the surface and the plate was stored at 35° C., 95 RH% for 24 hours. After zero hour from the initiation of the storage (theoretical number of added bacterial cells) and after storing the plate over 24 hours, the survival cells on the test specimen was washed off using a viable cell count-determining medium (SCDLP liquid medium), followed by determining the survival cells present in the wash liquid according to the pour plate culture method (at 37° C. for 2 days) using viable cell count-determining medium, normal agar medium and conversion of the result obtained into the viable cell count per plate of 5 cm×5 cm.

The results of the foregoing test for antimicrobial properties thus obtained are summarized in the following Table 3. In this respect, the initial number of bacterial cells was

TABLE 1

| Sample No. | ZnO | $B_2O_3$ | $P_2O_5$ | $Al_2O_3$ | $ZrO_2$ | $Na_2O$ | $SiO_2$ | Remarks |
|---|---|---|---|---|---|---|---|---|
| α1 | 59 | 0 | 30 | 5 | 0 | 6 | 0 | — |
| α2 | 55 | 28 | 0 | 1 | 0 | 7 | 9 | — |
| α3 | 54 | 0 | 25 | 0 | 3 | 8 | 10 | — |
| α4 | 57 | 30 | 0 | 0 | 2 | 7 | 4 | — |
| α5 | 50 | 40 | 0 | 0 | 0 | 0 | 10 | — |
| α6 | 50 | 30 | 0 | 0 | 0 | 10 | 10 | — |
| α7 | 50 | 0 | 30 | 0 | 4 | 1 | 15 | — |
| α8 | 30 | 60 | 0 | 0 | 0 | 10 | 0 | — |
| α9 | 55 | 28 | 0 | 1 | 0 | 7 | 9 | Surface Treatment |

Test Example 1
(Test for Color Change, Test for Antimicrobial Properties and Test for Water Resistance)

Each antimicrobial agent (Sample Nos. α1 to α4 and α9: 0.3% by weight) was blended with a polystyrene resin (trade name: ST850) available from Sumitomo Chemical Co., Ltd., followed by injection molding of the resulting blend at 220° C. using an injection-molding machine: M-50AII-DM available from Meiki Manufacturing Co., Ltd. to give each corresponding antimicrobial plate (11 cm×11 cm×2 mm) (Sample Nos. α1 to α3)(In this respect, the sample number of each antimicrobial plate is the same as that used for the sample number of the antimicrobial agent used; the same rule applies correspondingly to the following). In addition, the degree of discoloration was evaluated as follows: each $2.5\times10^5$. The number of bacterial cells observed for the control liquid was found to be $8.3\times10^5$ after 24 hours. In this respect, the control test was carried out by repeating the same procedures used above except for using only the bacteria-containing liquid without using any sample plate.

Samples of various kinds of polypropylene plates molded in the same manner used for preparing Sample Nos. α1 to α10 except for using a polypropylene resin (trade name: J105H available from Grand Polymer Co., Ltd.) instead of the foregoing polystyrene resin were immersed in warmed water of 90° C. for one week to determine the appearance of these plates and the antimicrobial powers of these plates were confirmed after immersing them in warmed water of 50° C. for 16 hours, to thus evaluate the water resistance thereof.

TABLE 2

| Antimicrobial Plate, Sample No. | Evaluation of Antimicrobial power (viable cell count) | Evaluation of Color Change (color of plate) | Evaluation of Antimicrobial Power after Warmed Water Test (viable cell count) | Evaluation of Water resistance (appearance of plate) |
|---|---|---|---|---|
| α1 | <10 | No Color Change | <10 | No Change |
| α2 | <10 | No Color Change | <10 | No Change |
| α3 | <10 | No Color Change | <10 | No Change |
| α4 | <10 | No Color Change | <10 | No Change |
| α5 | $8.6 \times 10^3$ | No Color Change | $7.7 \times 10^5$ | No Change |
| α6 | <10 | Changed to Pale Yellow | $1.9 \times 10^3$ | Whitening |
| α7 | $2.2 \times 10^4$ | No Color Change | $4.3 \times 10^4$ | No Change |
| α8 | $1.5 \times 10^5$ | Changed to Pale Yellow | $5.5 \times 10^5$ | Whitening |
| α9 | <10 | No Color Change | <10 | No Change |
| α10 | $7.2 \times 10^5$ | No Color Change | $6.8 \times 10^5$ | No Change |

The antimicrobial plates (Sample Nos. α1 to α4 and Sample No. α9) to which the antimicrobial agent of the present invention is added are excellent in all of the antimicrobial properties, resistance to color change and water resistance.

The antimicrobial plate (Sample No. α5) containing an antimicrobial agent, which consists of glass free of any alkali metal oxide, $Al_2O_3$, and $ZrO_2$ among the glass components used in the present invention is excellent in the resistance to color change and water resistance, but is insufficient in the antimicrobial properties. In addition, the antimicrobial plate (Sample No. α6) containing an antimicrobial agent, which consists of glass containing an alkali metal oxide, but free of $Al_2O_3$, and $ZrO_2$ is excellent in the antimicrobial properties, but insufficient in the resistance to color change and water resistance.

Furthermore, the antimicrobial plate (Sample No. α7) containing an antimicrobial agent, which consists of glass having an alkali metal oxide content of not more than 5 mole % is excellent in the resistance to color change and water resistance, but insufficient in the antimicrobial properties. In addition, the antimicrobial plate (Sample No. α8) containing an antimicrobial agent, which consists of glass having a molar ratio of ZnO incorporated therein smaller than that defined by the present invention is inferior in the antimicrobial properties, resistance to color change and water resistance.

Example 2
(Preparation of Antimicrobial Agent (Type β))

Each raw preparation (antimicrobial agents A to D) having a composition specified in the following Table 3 was melted with heating at 1000 to 1400° C., followed by cooling the molten preparation to give glass, and then pulverization thereof in a ball mill into glass particles having an average particle size of about 4 μm and a maximum particle size of 20 μm to give each corresponding antimicrobial agent consisting of glass particles.

Example 3
(Preparation of Surface-treated Antimicrobial Agent (Typed β))

The antimicrobial agent A prepared in Example 2 (5 kg) was introduced into a Henschel mixer, followed by spraying the agent with 200 g of an ethanol solution containing 50 g of γ-aminopropyl trimethoxysilane with stirring, removal of the sprayed antimicrobial agent A from the mixer and then subjecting it to a heat-treatment at 120° C. for 12 hours to complete the surface treatment of the agent (antimicrobial agent E).

Comparative Example 2
(Preparation of Antimicrobial Agent)

The same procedures used in Example 2 were repeated except for using each raw preparation having a composition specified in Table 3 to give each corresponding antimicrobial agent (antimicrobial agents F to I).

Separately, the same procedures used in Example 2 were repeated except for using a raw preparation having the composition specified in Table 3 (antimicrobial agent J), but the raw preparation never underwent any vitrification.

TABLE 3

| Ex. No. | A.A.* | Composition of Glass (mole %) | | | | | | | Remarks |
|---|---|---|---|---|---|---|---|---|---|
| | | ZnO | $P_2O_5$ | $Al_2O_3$ | $SnO_2$ | $Na_2O$ | $SiO_2$ | $B_2O_3$ | |
| 2 | A | 60 | 25 | 5 | 4 | 6 | 0 | 0 | |
| | B | 55 | 25 | 6 | 4 | 8 | 2 | 0 | |
| | C | 53 | 30 | 4 | 2 | 6 | 5 | 0 | |
| | D | 65 | 20 | 7 | 2 | 6 | 0 | 0 | |
| 3 | E | 60 | 25 | 5 | 5 | 5 | 0 | 0 | 1) |
| 2** | F | 45 | 25 | 5 | 5 | 5 | 15 | 0 | 2) |
| | G | 60 | 25 | 5 | 5 | 0 | 5 | 0 | 3) |
| | H | 60 | 0 | 0 | 0 | 5 | 10 | 25 | 4) |

TABLE 3-continued

| Ex. No. | A.A.* | Composition of Glass (mole %) | | | | | | | Remarks |
| --- | --- | --- | --- | --- | --- | --- | --- | --- | --- |
| | | ZnO | $P_2O_5$ | $Al_2O_3$ | $SnO_2$ | $Na_2O$ | $SiO_2$ | $B_2O_3$ | |
| | I | 50 | 20 | 2 | 2 | 20 | 6 | 0 | 5) |
| | J | 60 | 30 | 0 | 0 | 5 | 5 | 0 | 6) |

*: A.A. = antimicrobial agent
**: Comparative Example
1) The surface-treated antimicrobial agent is used.
2) The content of ZnO and $SiO_2$ does not fall within the scope of the present invention.
3) The content of $Na_2O$ does not fall within the scope of the present invention.
4) The content of $P_2O_5$, $Al_2O_3$, $SnO_2$ and $SiO_2$ does not fall within the scope of the present invention.
5) The content of $Na_2O$ and $SiO_2$ does not fall within the scope of the present invention.
6) This preparation never undergoes any vitrification.

Test Example 2

To 100 parts by weight of a mixed syrup containing poly(methyl methacrylate) and methyl methacrylate (weight ratio: 2/8), there was added 150 parts by weight of aluminum hydroxide. There were further added, to the mixture, 0.7 part by weight of a curing agent (ethylene glycol dimethacrylate) and 0.6 part by weight of a curing-accelerator (tertbutylperoxy maleic acid) to give a resin composition for artificial marble. Then 1.0 part by weight of each antimicrobial agent (antimicrobial agents A to I) prepared in Example 2 or 3 or Comparative Example 2 was added to 100 parts by weight of the resin composition, followed by mixing them. The composition was poured into a mold, cured at room temperature and released from the mold to give a molded body of artificial marble (Sample Nos. β1 to β9).

By way of comparison, an artificial marble molded body was prepared without adding any antimicrobial agent (Sample No. β10).

The colors of the molded bodies thus produced were visually confirmed to evaluate the appearance thereof.

In addition, the antimicrobial powers of the resulting molded bodies were evaluated by the following method.

Staphylococcus aureus was used as test bacteria, a specimen having a size of 5 cm×5 cm was cut from each molded body of the antimicrobial artificial marble, a liquid containing the bacteria (0.5 ml) was dropped on the surface of each specimen of the marble so that the number of bacterial cells per specimen was equal to $10^5$ to $10^6$. Then the surface of the specimen was covered with a polyethylene film of 4.5 cm×4.5 cm to thus uniformly bring the surface into contact with the film and the specimen was stored at 35° C., 95RH % for 24 hours. After zero hour from the initiation of the storage (theoretical number of added bacterial cells) and after storing the specimen for 24 hours, the survival cells on the test specimen was washed off using a viable cell count-determining medium (SCDLP liquid medium), followed by determining the survival cells present in the wash liquid according to the plate culture method (at 37° C. for 2 days) using a normal agar medium conversion of the result obtained into the viable cell count per plate of 5 cm×5 cm. In this respect, the initial number of bacterial cells was $2.2 \times 10^5$ and the number of bacterial cells observed for the control after 24 hours was found to be $2.5 \times 10^5$. In this case, the control test was carried out by repeating the same procedures used above without using any sample.

Moreover, each specimen was immersed in warmed water of 50° C. for 500 hours and the appearance thereof was evaluated. In addition, the antimicrobial power of each specimen was evaluated after immersing it in warmed water of 90° C. for 16 hours. The results of the foregoing tests are summarized in the following Table 4.

TABLE 4

| Sample No. | Antimicrobial Agent | Evaluation of Antimicrobial Power (viable cell count) | Appearance Test | Evaluation of Antimicrobial Power* (viable cell count) | Appearance Test** |
| --- | --- | --- | --- | --- | --- |
| β1 | A | <10 | Good | <10 | Good |
| β2 | B | <10 | Good | <10 | Good |
| β3 | C | <10 | Good | <10 | Good |
| β4 | D | <10 | Good | <10 | Good |
| β5 | E | <10 | Good | <10 | Good |
| β6 | F | $3.2 \times 10^3$ | Good | $2.0 \times 10^5$ | Good |
| β7 | G | $7.5 \times 10^3$ | Good | $1.8 \times 10^4$ | Good |
| β8 | H | <10 | Good | $9.0 \times 10^4$ | Whitening, Rough Surface |
| β9 | I | <10 | Good | <10 | Rough Surface |
| β10 | None | $1.8 \times 10^5$ | Good | $1.5 \times 10^5$ | Good |

*: Evaluation of antimicrobial power after warmed water test.
**: Appearance test after warmed water test.

The antimicrobial plate to which the antimicrobial agent of the present invention is added (Sample Nos. β1 to β5) exhibits excellent antimicrobial properties, resistance to color change and water resistance.

The antimicrobial plate (Sample No. β6), which contains an antimicrobial agent whose content of ZnO is low and the antimicrobial plate (Sample No. β7), which contains an antimicrobial agent free of any alkali metal oxide are excellent in the water resistance and resistance to color change, but are insufficient in the antimicrobial properties. Moreover, the antimicrobial plate (Sample No. β8), which contains an antimicrobial agent free of $P_2O_5$, $Al_2O_3$ and $SnO_2$ does not suffer from any problem immediately after molding, but the antimicrobial properties thereof is reduced and the appearance thereof is impaired, after the warmed water test.

The antimicrobial plate (Sample No. β9), which contains an antimicrobial agent containing not less than 10 mole % of an alkali metal oxide becomes rough after the warmed water test and therefore, it is inferior in the water resistance.

Test Example 3

To 100 parts by weight of an isophthalic acid type unsaturated polyester resin, which is blended with 60% by weight of silica fine particles, there was added 1.0 part by weight of each antimicrobial agent (antimicrobial agents A to I) prepared in Example 2, 3 or Comparative Example 2, followed by admixing them. To the resulting mixture, there were added 1.5 part by weight of methyl ethyl ketone peroxide as a curing agent and 1.0 part by weight of cobalt naphthenate as a curing accelerator to give a paint composition for a gel coat layer.

The foregoing paint composition was applied onto the interior of a mold for molding with a spray gun so that the thickness of the applied composition was about 0.5 mm and cured at room temperature. Subsequently, there was poured into the mold a base resin composition mainly comprising an isophthalic acid type unsaturated polyester resin, which contained 50% by weight of aluminum hydroxide, followed by curing the resin at room temperature and removal of the molded body from the mold to give an artificial marble product carrying a gel coat layer (Sample Nos. β11 to β19).

By way of comparison, the same procedures used above were repeated except that the addition of an antimicrobial agent was omitted to give an artificial marble product (Sample No. β20).

The colors of the surfaces of the gel coat layers on the resulting artificial marble products were visually confirmed to evaluate the appearance thereof.

In addition, the antimicrobial powers of the surfaces of the gel coat layers on the resulting artificial marble products were evaluated by the following method.

Staphylococcus aureus was used as test bacteria, a specimen having a size of 5 cm×5 cm was cut from each molded body of the antimicrobial artificial marble, a liquid containing the bacteria (0.5 ml) was dropped on the surface of each specimen of the marble so that the number of bacterial cells per specimen was equal to $10^5$ to $10^6$. Then the surface of the specimen was covered with a polyethylene film of 4.5 cm×4.5 cm to thus uniformly bring the surface into contact with the film and the specimen was stored at 35° C., 95RH % for 24 hours. After zero hour from the initiation of the storage (theoretical number of added bacterial cells) and after storing the specimen for 24 hours, the survival cells on the test specimen was washed off using a viable cell count-determining medium (SCDLP liquid medium), followed by determining the survival cells present in the wash liquid according to the pour plate culture method (at 37° C. for 2 days) using a normal agar medium and conversion of the result obtained into the viable cell count per plate of 5 cm×5 cm. In this respect, the initial number of bacterial cells was $2.2 \times 10^5$ and the number of bacterial cells observed for the control after 24 hours was found to be $2.5 \times 10^5$. In this case, the control test was carried out by repeating the same procedures used above without using any sample.

Moreover, each specimen was immersed in warmed water of 50° C. for hours and the appearance thereof was evaluated. In addition, the antimicrobial power of each specimen was evaluated after immersing it in warmed water of 90° C. for 16 hours. The results of the foregoing tests are summarized in the following Table 5.

TABLE 5

| Sample No. | Antimicrobial Agent | Evaluation of Antimicrobial Power (viable cell count) | Appearance Test | Evaluation of Antimicrobial Power* (viable cell count) | Appearance Test** |
|---|---|---|---|---|---|
| β11 | A | <10 | Good | <10 | Good |
| β12 | B | <10 | Good | <10 | Good |
| β13 | C | <10 | Good | <10 | Good |
| β14 | D | <10 | Good | <10 | Good |
| β15 | E | <10 | Good | <10 | Good |
| β16 | F | $5.5 \times 10^2$ | Good | $6.4 \times 10^4$ | Good |
| β17 | G | $1.2 \times 10^3$ | Good | $8.4 \times 10^4$ | Good |
| β18 | H | <10 | Good | $2.8 \times 10^3$ | Whitening, Rough Surface |
| β19 | I | <10 | Pale Yellow | <10 | Yellowing, Rough Surface |
| β20 | None | $1.0 \times 10^5$ | Good | $1.2 \times 10^5$ | Good |

*: Evaluation of antimicrobial power after warmed water test.
**: Appearance test after warmed water test.

The antimicrobial plate to which the antimicrobial agent of the present invention is added (Sample Nos. β11 to β15) exhibits excellent antimicrobial properties, resistance to color change and water resistance.

The antimicrobial plate (Sample No. β16), which contains an antimicrobial agent whose content of ZnO is low and the antimicrobial plate (Sample No. β17), which contains an antimicrobial agent free of any alkali metal oxide are excellent in the water resistance and resistance to color change, but is insufficient in the antimicrobial properties. Moreover, the antimicrobial plate (Sample No. β18), which contains an antimicrobial agent free of $P_2O_5$, $Al_2O_3$ and $SnO_2$ does not suffer from any problem concerning the antimicrobial properties and resistance to color change immediately after molding, but the antimicrobial properties thereof is reduced, the appearance thereof is impaired and the water resistance is reduced, after the warmed water test.

The antimicrobial plate (Sample No. β19), which contains an antimicrobial agent containing not less than 10 mole % of an alkali metal oxide has good resistance to color change immediately after the molding, but becomes rough surface, undergoes color change and is inferior in the water resistance, after the warmed water test.

What is claimed is:

1. An antimicrobial agent consisting of glass which comprises 50 to 60 mole % of ZnO, 20 to 30 mole % of at least one member selected from the group consisting of $B_2O_3$ and $P_2O_5$, 1 to 10 mole % of at least one member selected from the group consisting of $Al_2O_3$ and $ZrO_2$, 5 to 10 mole % of an alkali metal oxide and 0 to 15 mole % of $SiO_2$.

2. The antimicrobial agent of claim 1 which consists of glass which comprises 53 to 60 mole % of ZnO, 20 to 30 mole % of at least one member selected from the group consisting of $B_2O_3$ and $P_2O_5$, 1 to 10 mole % of at least one member selected from the group consisting of $Al_2O_3$ and $ZrO_2$, 6 to 8 mole % of an alkali metal oxide and 0 to 15 mole % of $SiO_2$.

3. The antimicrobial agent of claim 1 wherein the alkali metal oxide is $Na_2O$.

4. An antimicrobial resin composition comprising an antimicrobial agent as set forth in claim 1 and a resin.

5. The antimicrobial resin composition of claim 4, wherein the rate of the added antimicrobial agent ranges from 0.01 to 10 parts by weight per 100 parts by weight of the antimicrobial resin composition.

6. Antimicrobial artificial marble comprising an antimicrobial agent as set forth in claim 1 and a (meth)acrylic resin or an unsaturated polyester resin.

7. Antimicrobial artificial marble having an antimicrobial gel coat layer on the surface of a base resin, wherein said antimicrobial gel coat layer comprises an antimicrobial agent as set forth in claim 1 and a (meth)acrylic resin or an unsaturated polyester resin.

8. An antimicrobial agent comprising glass which comprises 50 to 60 mole % of ZnO, 20 to 30 mole % of at least one member selected from the group consisting of $B_2O_3$ and $P_2O_5$, 1 to 10 mole % of at least one member selected from the group consisting of $Al_2O_3$ and $ZrO_2$, 5 to 10 mole % of an alkali metal oxide and 0 to 15 mole % of $SiO_2$.

9. An antimicrobial agent consisting of glass which comprises 50 to 70 mole % of ZnO, 20 to 35 mole % of $P_2O_5$, 0.5 to 10 mole % of $Al_2O_3$, 0.5 to 10 mole % of $SnO_2$, 0 to 5 mole % of $SiO_2$ and 5 to 10 mole % of an alkali metal oxide.

10. The antimicrobial agent of claim 9, which consists of glass which comprises 53 to 65 mole % of ZnO, 25 to 30 mole % of $P_2O_5$, 2 to 7 mole % of $Al_2O_3$, 2 to 7 mole % of $SnO_2$, 0 to 5 mole % of $SiO_2$ and 6 to 8 mole % of an alkali metal oxide.

11. The antimicrobial agent of claim 9 wherein the alkali metal oxide is $Na_2O$.

12. An antimicrobial resin composition comprising an antimicrobial agent as set forth in claim 9 and a resin.

13. The antimicrobial resin composition of claims 12, wherein the rate of the added antimicrobial agent ranges from 0.01 to 10 parts by weight per 100 parts by weight of the antimicrobial resin composition.

14. Antimicrobial artificial marble comprising an antimicrobial agent as set forth in claim 9 and a (meth)acrylic resin or an unsaturated polyester resin.

15. Antimicrobial artificial marble having an antimicrobial gel coat layer on the surface of a base resin, wherein said antimicrobial gel coat layer comprises an antimicrobial agent as set forth in claim 9 and a (meth)acrylic resin or an unsaturated polyester resin.

16. An antimicrobial agent comprising glass which comprises 50 to 70 mole % of ZnO, 20 to 35 mole % of $P_2O_5$, 0.5 to 10 mole % of $Al_2O_3$, 0.5 to 10 $SnO_2$, 0 to 5 mole % of $SiO_2$ and 5 to 10 mole % of an alkali metal oxide.

* * * * *